(12) United States Patent
Riley

(10) Patent No.: US 9,265,792 B2
(45) Date of Patent: Feb. 23, 2016

(54) INTEGUMENT CELL REGENERATION FORMULATION

(76) Inventor: Patricia A. Riley, Golden Beach, FL (US)

( * ) Notice: Subject to any disclaimer, the term of this patent is extended or adjusted under 35 U.S.C. 154(b) by 736 days.

(21) Appl. No.: 11/560,567

(22) Filed: Nov. 16, 2006

(65) Prior Publication Data

US 2007/0110731 A1    May 17, 2007

Related U.S. Application Data

(60) Provisional application No. 60/597,204, filed on Nov. 16, 2005.

(51) Int. Cl.
| | |
|---|---|
| *A61K 31/728* | (2006.01) |
| *A61K 38/18* | (2006.01) |
| *A61Q 19/08* | (2006.01) |
| *A61K 36/00* | (2006.01) |
| *A61K 36/15* | (2006.01) |
| *A61K 36/45* | (2006.01) |
| *A61K 36/73* | (2006.01) |
| *A61K 36/82* | (2006.01) |
| *A61K 36/87* | (2006.01) |
| *A61K 36/8962* | (2006.01) |
| *A61K 8/98* | (2006.01) |

(52) U.S. Cl.
CPC .............. *A61K 31/728* (2013.01); *A61K 8/982* (2013.01); *A61K 36/15* (2013.01); *A61K 36/45* (2013.01); *A61K 36/73* (2013.01); *A61K 36/82* (2013.01); *A61K 36/87* (2013.01); *A61K 36/8962* (2013.01); *A61K 38/18* (2013.01); *A61K 38/1825* (2013.01); *A61Q 19/08* (2013.01)

(58) Field of Classification Search
CPC . A61K 31/728; A61K 38/18; A61K 38/1825; A61Q 19/08
See application file for complete search history.

(56) References Cited

U.S. PATENT DOCUMENTS

| | | | |
|---|---|---|---|
| 5,604,200 A * | 2/1997 | Taylor-McCord | 514/8 |
| 2003/0105007 A1* | 6/2003 | Beaulieu et al. | 514/12 |
| 2006/0078993 A1* | 4/2006 | Phan et al. | 435/366 |
| 2007/0224150 A1* | 9/2007 | Chung | 424/70.14 |

FOREIGN PATENT DOCUMENTS

WO    WO 2005062791 A2 *    7/2005

* cited by examiner

*Primary Examiner* — Taeyoon Kim
(74) *Attorney, Agent, or Firm* — Buckingham, Doolittle & Burroughs, LLC

(57) ABSTRACT

The invention relates to a composition-of-matter and method of using a topical composition having 10-99.999% by weight of a topical base formulation and other active ingredients including stem cell or growth factors and/or antioxidants, as well as others for the purpose of regenerating integument cells.

17 Claims, No Drawings

INTEGUMENT CELL REGENERATION FORMULATION

TECHNICAL FIELD

This invention relates to formulations which help to regenerate integument cells, reversing signs of aging and wrinkling of the skin and regenerate new cells in the dermis, epidermis, and connective tissue.

BACKGROUND OF THE INVENTION

Wrinkles are signs of aging and photodamage that occur with time. Since the beginning of time a search has been made for ways to reduce wrinkles and make the skin look younger. Plastic surgery, Botox™ and injections of collagen, hyaluronic acid and other substances have been used to smooth wrinkles. Wrinkle creams have been formulated incorporating lubricating elements such as emollients, moisturizing ingredients such as hyaluronic acid, silicones, vitamins, and other skin smoothing agents.

SUMMARY OF THE INVENTION

Accordingly it is a principal object of the invention to develop a formulation or method to naturally regenerate integument cells (hair, skin, and nail cells). The formulation reduces signs of aging on the skin and assists in wound healing. The formulation reduces the look of expression lines and wrinkles and to make the skin look younger.

In one embodiment a composition has been developed that is capable of smoothing coarse deep expression lines and wrinkles with a measurable increase in spacing between wrinkles; a smoothing of the skin surface; and a reduction in the number of wrinkles.

The formula was designed, among other reasons, to deliver hyaluronic acid in a liposome with specific peptides and botanicals in an effort to "reverse age engineer" the appearance of the skin. The benefit of this formulation is the smoothing of the appearance of expression lines and wrinkles, and to stimulate the collagen matrix for smoother, firmer younger looking skin.

The use of specific peptides combined with hyaluronic acid in a liposome delivery system is able to achieve a plumping of the skin and a relaxing effect of the wrinkles at the same time.

Clinical observation showed the formulation dramatically improved the appearance of the skin, rapidly reducing the look of stubborn lines and wrinkles in expression zones of the face: the forehead, midbrow, above mouth, sides of mouth, crows feet.

The invention further includes a method for reducing the look of wrinkles, creases, and expression lines as well as a method for applying a composition and following with water to swell the hyaluronic liposomes to plump the skin smoothing the appearance of lines and wrinkles and a method for increasing penetration of cartilage and collagen rebuilding matrix proteins.

These and other objects of the present invention will become more readily apparent from a reading of the following detailed description taken in conjunction with the appended claim.

DETAILED DESCRIPTION OF THE INVENTION

Collagen and elastin fibers allow your skin to move, stretch and recover its original smooth appearance. Between the fibers is a vital protein-sugar matrix comprised of glycosaminoglycans. This delicate reservoir supplies vital nutrients and hormones to the skin cells. With aging the level of glycosominoglycans decrease. Glycosaminoglycans include hyaluronic acid, chondroitin sulfate A, chondroitin sulfate C, dermatan sulfate, heparin, keratan sulfate, keratosulfate, chitin, chitosan 1, and chitosan.

Hyaluronan (also known as hyaluronic acid or hyaluronate) (HA), is a glycosaminoglycan lacking a protein core, and is one of the major non-structural elements of the extracellular matrix. Hyaluronic acid and salts play key roles in biological phenomena associated with cell motility including development, regeneration, repair, wound healing, angiogenesis, and immune responses.

A wrinkle can be defined as a rupture of elastic fibers and collagen fibers occurring in the epidermis and the dermis, combined with a quantitative reduction of dermal substances (glycosaminoglycans (GAGs), collagen . . . ) that increases with age. Starting at the age of 30 on average, the first lines appear on the surface of the skin but easily disappear after the skin is gently stretched mechanically.

There are several types of wrinkles that are distinguished either by their location or mechanism of formation, but all can be intensified by various intrinsic (hereditary, hormonal . . . ) or extrinsic factors (sun, pollution, tobacco . . . ). They are found primarily on the face (around the mouth, the eyes and on the forehead) and the hands, zones that are naturally exposed to the environment.

So-called expression wrinkles on the face are folds of varying depth that form when you knit your brows or smile. They form along the lines of natural tension of the skin (Langer's line) and no longer disappear when stretched since they arise from muscular contraction.

With increasing age, the fold remains the same and becomes definitive often along an orientation perpendicular to the underlying muscle layer. These folds are categorized as: forehead wrinkles—vertical or horizontal wrinkles on the forehead; frown lines, between the eyebrows; crow's feet wrinkles, at the contour of the eyes; naso-labial wrinkles around the lips; and wrinkles of the nasolabial fold, that form after a movement of the cheek that descends and causes a fold starting from the nose and descending along the mouth.

These wrinkles of the nasolabial fold are a good example of wrinkles due to ptosis, i.e. the downward placement of subcutaneous muscles and the skin covering them In plain language, these wrinkles appear when the skin loses its elasticity and is subjected to the force of gravity.

Expression lines are wrinkles arising from repeated and frequent movements, requiring the activity of sub-conjonctival muscle masses in the same direction (mimics of expression), accompanied by muscular laxity. Expression lines refer to a type of wrinkles caused by repeated facial movements that occur on a regular basis: smiling, frowning, laughing, and talking can all influence the gradual deepening of expression lines on the face. Recently peptides have been engineered to reduce expression wrinkles by modifying signaling pathways to superficial muscles, thereby reducing the creasing of the skin and the appearance of expression lines.

Depending on their location, the depth of these expression wrinkles can vary, but they are consistently more pronounced than other types of wrinkles (around the mouth or the neckline), that although clearly finer are nevertheless a sign of advancing age.

Causative or aggravating agents are often environmental factors such as the sun, tobacco, alcohol, pollution or insufficient skin care.

Liposomes are hollow spheres of lipid double membranes with the hydrophilic parts of the lipids orientated to the inner and outer surfaces of the membranes. There can also be several double membranes separated from each other by aqueous phases, hence a distinction is made between uni- and multi-lamellar lipid vesicles. Typically, liposomes are between 0.02 and 10 micrometers in size. They are also characterized by their lipid composition, their morphology and their charge, size and size distribution, lamellarity and lamellarity distribution are not thereby merely a function of the lipids used, they are also particularly affected by the method of preparation employed. Amphiphilic liquids, that are lipids with lipophilic and hydrophilic portions, are necessary components of liposomes. Phospholipids (phosphatidylcholine, phosphatidylthanolamine, phosphatidic acid, phosphatidylserine and phosphatidylinositol) are very important in this respect since they are the building blocks of animal cells. The types of liposomes finding application in cosmetics include alongside phospholipid liposomes, sphingosomes with sphingolipids (e.g. ceramides) as essential components and niosomes, which are hollow spheres formed from noniongenic detergents (e.g. polyoxyethylene alkyl ethers, polyoxyethylene alkyl esters or sucrose diesters).

Liposomes can be loaded with drugs, vitamins, care agents and compounds with sun-protection properties. Hydrophilic substances are transported in the aqueous phase within the hollow shell, while substances with lipophilic properties can be directly integrated into the lipid double layer. Liposomes then become transport vesicles in addition to their other properties. Here the molecular size and chemical structure of the molecule to be transported also help determine, along with the specific properties of the liposome, if and to what extent drugs and care agents are enriched to a greater extent in the horny layer, reach the epidermal basal cells and pass into the dermal microcirculation and hence, are able to bring about systemic effects. The discovery and development of liposomal dosage forms with quite specific properties is the subject of current scientific research and presents a challenge to the cosmetics industry and to that part of the pharmaceutical industry specializing in dermatological products.

Peptides are specific links of amino acids—the basic subunits of protein. Amino acids link together in long chains for constructing protein. Peptides are the primary linkage of all protein structures; the chemical bond between the carboxyl groups and amino groups that unites a peptide is a peptide linkage. Recently, peptides have been developed which may help to signal skin fibroblasts to create collagen and elastin skin cells, improving elasticity and firmness. Common peptides that may be added to various embodiments of this invention include but are not limited to Acetyl Hexapeptide-8, Acetyl Tetrapeptide-5, Pentapeptide-3, Hydrolyzed, Vegetable Protein, Tripeptide-3, Hexapeptide-10, Acetyl Glutamyl Hexapeptide-6, Acetyl Glutamyl Hexapeptide-3, Pamitoyl Tripeptide-5, Dipeptide Diaminobutyrooyl Benzylamide Diacetate, Pentapeptide-3, Tripeptide-1, Acetyl Tetrapeptide-2, Acetyl Hexapeptide-1, Nonapeptide-1, Tripeptide-2, Hexapeptide-11, Dipeptide-2, Carnosine, Palmitoyl, Oligopeptide, Palmitoyl Tetrapeptide-7, Cottonseed Peptide, Sweet Almond Peptide.

It is known that hyaluronic acid smoothes the skin and decreases roughness by holding a thousand times its weight in moisture. Its plumping effect on the skin is well known. It is also known that liposomes are lecithin-based carriers of active compounds in the skin. Due to their chemical structure, the skin absorbs liposomes and their contents readily. The science of creating liposomes to carry cosmetics into the skin, such as vitamins, is well recognized.

The invention at hand is comprised of various compositions, compounds, and elements as described below, combined in a topical base for application to a user's skin. The composition of the invention at hand consists of at least approximately 10% of topical base by weight The remainder of the formulation of this invention is comprised of the active ingredients described within this specification. In certain embodiments of this invention the topical base may comprise the vast majority of the weight of the formulation as the active ingredients are so potent as to require only minimal amounts to be effective. For example, it is foreseen by this invention that the topical base may comprise up to 99.999% by weight of the formula, with active ingredients only comprising 0.001% by weight to 90%.

The topical formulation of this invention is not limited to any one particular topical base, but can utilize any topical base known within the art of skin care. The topical base may be a lotion, serum, liquid, cream or other topical base known in the art. Non-limiting examples of topical base formulations that may be used in the composition of this invention commonly include glycerine, triglyceride, natural butters, oils or waxes in combinations to form a lotion, cream, liquid, solvent or other topical base for application to the skin. Colorings and or fragrances may also be added to the topical formulation.

The formulation of one embodiment of the invention is a complex advanced formula that combines 3 novel peptides: Acetyl Hexapeptide-3, Palmitoyl Tripeptide-3 and Acetyl Glutamyl Heptapeptide-1 with liposomal hyaluronic acid, ceramide 3, and antioxidant vitamins A, C, E. The formula also contains botanicals that act as antioxidants including, but not limited to Pine Bark Extract, and Sea Whip Extract. In addition the formulation contains Sacred Lotus Seed extract that has been shown to be a natural source of a repair enzyme that enables the seed to resist aging and live over 1200 years.

In further embodiments of this invention various peptides may be used. Examples of useful peptides that may be utilized in certain embodiments of this invention, include but are not limited to; Acetyl Hexapeptide-8, Acetyl Tetrapeptide-5, Pentapeptide-3, Hydrolyzed, Vegetable Protein, Tripeptide-3, Hexapeptide-10, Acetyl Glutamyl Hexapeptide-6, Acetyl Glutamyl Hexapeptide-3, Pamitoyl Tripeptide-5, Dipeptide Diaminobutyrooyl Benzylamide Diacetate, Pentapeptide-3, Tripeptide-1, Acetyl Tetrapeptide-2, Acetyl Hexapeptide-1, Nonapeptide-1, Tripeptide-2, Hexapeptide-11, Dipeptide-2, Carnosine, Palmitoyl, Oligopeptide, Palmitoyl Tetrapeptide-7, Cottonseed Peptide, Sweet Almond Peptide.

In another embodiment of the invention, because hyaluronic acid is vital to the collagen and cartilage support matrix such a composition may also stimulate collagen and cartilage tissue and be a method to reduce the symptoms of arthritis, swelling and joint pain, and to stimulate new tissue growth stimulate collagen and cartilage tissue.

What is shown is a composition that combines hyaluronic acid (preferably liposomal) plus at least one vitamin, including Vitamin A, $B_1$, $B_2$, $B_3$, $B_5$, $B_6$, $B_{12}$, panthenol, vitamin C, vitamin D and, or vitamin E, beta carotene, lycopene, lutein, alpha lipoic acid or coenzyme Q10 The composition can additionally contain paimitoyl tripeptide-3, plus acetyl hexapeptide-3, acetyl glutamyl heptaptide-1 in liposomes or simply added to the composition.

The composition of certain embodiments may combine hyaluronic acid (preferably liposomal) plus any two peptides (also preferably in liposomes although they may be simply added to the composition) from the list including palmitoyl tripeptide-3, acetyl hexapeptide-3, palmitoyl oligopeptide, palmitoyl pentapeptide 3, acetyl glutamyl heptaptide-1, tripeptide, marine collagen polypeptides or hexapeptide 11 Any two peptides outlined above may be combined with any glycosaminoglycan, including hyaluronic acid, chondroitin sulfate A, chondroitin sulfate C, dermatan sulfate, heparin, keratan sulfate, keratosulfate, chitin, chitosan 1, and chitosan either in liposomal form or in the general composition.

In another embodiment, the composition will combine liposomal hyaluronic acid plus nutrients also in liposomes or simply added to the composition, including but not limited to Vitamin A, $B_1$, $B_2$, $B_3$, $B_5$, $B_6$, $B_{12}$, panthenol, beta carotene, lycopene, lutein, zeaxanthin, vitamin C (ascorbic acid), ascorbyl palmitate, sodium ascorbyl phosphate, calcium ascorbate, magnesium ascorbyl phosphate, vitamin D, or vitamin E plus at least one peptide.

In yet another embodiment, the composition will be comprised of antioxidants also in liposomes or simply added to the composition, including but not limited to tocotrienols, Coenzyme Q 10, alpha lipoic acid, carnosine, carnitine, superoxide disumutase, catalase, pine bark, grape seed, green tea, Gorgonian extract, and their chemical equivalents. It is also foreseen to optionally include colostrums derived from cows, goats, sheep or other mammals in liposomes or simply added to the composition or even psudoaltermonas ferment glycoprotein, ectoin, plus other peptides or fibroblast growth factors. The composition of this embodiment will further include one or more of the following growth factors, including but not limited to Epidermal Growth Factor, Insulin-like Growth Factor, Acidic Fibroblast Growth Factor, Basic Fibroblast Growth Factor, Keratinocyte Growth Factor, Interleukin-10, Stem Cell Factor, Transforming Growth Factor, Platelet Derived Growth Factor, and Vascular Endothelial Growth Factor.

It is also part of the invention that the formulation include amino acid or combination of amino acids such as alanine, arginine, aspartate, asparagine, cysteine, glycine, lysine, valine, leucine, histidine, methionine, proline, serine, ornithine, glutamine, ornithine, tyrosine, tryptophane, also in liposomes or simply added to the composition as well as one or a combination of growth factors including Epidermal Growth Factor, Insulin-like Growth Factor, Acidic Fibroblast Growth Factor, Basic Fibroblast Growth Factor, Keratinocyte Growth Factor, Interleukin-10, Stem Cell Factor, Transforming Growth Factor, Platelet Derived Growth Factor, and Vascular Endothelial Growth Factor.

It is possible that the liposomes are substituted with nanospheres, smaller molecules which assist delivery of key substances.

A preferred embodiment of this invention may include the combination of liposomal or nanospherical antioxidants, and one or more growth factors. The antioxidants may include, but are not limited to, tocotrienols, Coenzyme Q 10, alpha lipoic acid, carnoside, carnitine, superoxide disumutase, catalase, pine bark, grape seed, green tea, or gorgonian extract. The growth factors may include, but are not limited to, epidermal growth factor, insulin-like growth factor, acidic fibroblast growth factor, basic fibroblast growth factor, keratinocyte growth factor, interleukin-10, stem cell factor, transforming growth factor, and vascular endothelial growth factor.

A further preferred embodiment of this invention may include from about 0.001-90% by weight of one or more active ingredients such as stem cells, stem cell factors, hyaluronan, epidermal growth factor, insulin-like growth factor, thioredoxin, keratinocyte growth factor, transforming growth factor, interleukin-10, platelet derived growth factor, vascular endothelial growth factor, acidic fibroblast growth factor, basic fibroblast growth factor, fibroblast growth factor-10, interleukin-4, homo sapiens noggin, thymosin, nerve growth factors, and human growth hormone added to the topical base. The active ingredients may be added to the base directly, or in liposomal or nanospherical form. Antioxidants may also be added to the composition, including but not limited to tocotrienols, coenzyme Q 10, alpha lipoic acid, carnosine, glutathione, superoxide disumutase, catalase, pine bark, grape seed, onion, blueberry, green tea, apple extract, and gorgonian extract.

Yet another preferred embodiment of this invention may include from about 10-99.999% by weight topical base formulation, and from about 0.001-90% by weight active ingredients. The active ingredients include 0.001% to about 89.999% by weight of stem cells or stem cell factors. The active ingredients will also include 0.001% to about 89.999% of at least one growth factor, including but not limited to hyaluronan, epidermal growth factor, insulin-like growth factor, thioredoxin, keratinocyte growth factor, transforming growth factor, interleukin-10, platelet derived growth factor, vascular endothelial growth factor, acidic fibroblast growth factor, basic fibroblast growth factor, fibroblast growth factor-10, interleukin-4, homo sapiens noggin, thymosin, nerve growth factors, and human growth hormone added to the topical base. The active ingredients may be added to the base directly, or in liposomal or nanospherical form. Antioxidants may also be added to the composition, including but not limited to tocotrienols, coenzyme Q 10, alpha lipoic acid, carnosine, glutathione, superoxide disumutase, catalase, pine bark, grape seed, onion, blueberry, green tea, apple extract, and gorgonian extract.

The formulation of this invention may be used to regenerate integument cells (hair, skin and nail cells). The formulation may be used to reduce signs of aging and assist in wound healing, including the reduction of scar tissue formation.

Various embodiments of this invention may include vitamins, such as but not limited to Vitamin A, Retinol, Vitamin $B_1$, Vitamin $B_2$, Vitamin $B_3$, Vitamin $B_5$, Vitamin $B_6$, Vitamin $B_{12}$, Panthenol, Vitamin C, Vitamin D, Vitamin E, Beta Carotene, Lycopene, and Lutein. Various embodiments of this invention may also include vitamins, such as but not limited to Alanine; Arginine; Aspartate; Asparagines; Cysteine; Glycine; Lysine; Valine; Leucine; Histidine; Methionine; Proline/Hydroxyproline; Serine; Ornithine; Glutamine; Ornithine; Tyrosine; and Tryptophane.

Additional components which may optionally be added to various embodiments of the formulation include *Nelumbu Nucifera* (Sacred Lotus) its seeds, roots, rhizomes, flower, petals, pistules or any part thereof, either combined or singly with Blue Lotus, White Lotus, Pink Lotus, Yellow Lotus their roots, seeds, rhizomes, flowers, petals, pistules, or any part thereof or additionally optionally combined with a hormone such as estrogen, estriol, estradiol, progesterone, pregenolone, testosterone, or their botanical mimics: phytoestrogens from soy, wild yam, *polygonum cuspidatum*.

It is still within the varying embodiments of the invention to optionally include traditional ingredients with any of the above to make the composition including glycerin, alpha hydroxy acids, lactic acid, glycolic acid, citric acid, malic acid, soybean oil, sunflower seed oil, safflower seed oil, palm oil, ginseng, rapeseed oil, avocado oil, lecithin, shea butter, squalane, xanthan gum propylene glycol, aloe, isopropyl myristate, cetyl alcohol, butylene glycol, *centella asiatica, echinacea purpurea*, glycol stearate, cocoa seed butter, ginseng, carbomer, ceramides, phenyl trimethicone, dimethicone, silicon, polysiloxilane, grape seed extract as well as with seaweeds and/or algea extracts, including but not limited to *Fucoidan, Laminaria Japonica, Gracileria Ferox, Laminaria Digitata, Caulerpa taxifolia* or their constituents.

Additional components that may optionally be added to various embodiments of this invention include sunscreen agent to the composition such as titanium dioxide, zinc oxide, octinoxate, octisalates, oxybenzone or Parsol 1789 or other UVA absorbers as well as mineral peptides, such as copper peptide, zinc peptide, selenium peptide, iron peptide, magnesium peptide, manganese peptide also in liposomes or simply added to the composition or algae extract, plus hydrolyzed rice protein also in liposomes or simply added to the composition.

Further additional components that may be optionally included are wheat peptide, oat peptide, plus soy peptide also in liposomes or simply added to the composition as well as acetyl glutamyl heptapeptide-1, plus acetyl hexapeptide-3, plus ectoin also in liposomes or simply added to the composition as well as Methylsulfonylmethane (MSM), S-adenosylmethionine, chondroitan sulfate, glucosamine, tumeric, menthol, keratin sulfate, chitin/chitosan or glutamine also in liposomes or simply added to the composition.

The advantages and important features of the present invention will be more apparent from the following examples which are given for illustrative purposes only to delineate some of the features of the invention and are not intended to be limiting. It is important to note that the composition of this invention does not require all ingredients listed in the examples. The ingredients listed are examples of a variety of ingredients which may or may not be included in varying embodiments of this invention. It is also important to note that the following lists are not inclusive of all of the ingredients that may be added to the formulation of this invention. Ingredients may be added that are not included in the below tables.

The quantities of the below ingredients are given in percent by approximate weight (% wt) or approximate units (IU) unless otherwise noted based on the total weight of the composition. The term qs means to use a sufficient quantity by weight to bring the entire composition to 100%. Whenever possible International Nomenclature Cosmetic Ingredient (INCI) names are used.

Further embodiments of the invention may include a number of ingredients, including but not limited to:

| Ingredient | Quantity (Range) | Preferred Quantity (Range) |
| --- | --- | --- |
| Water | qs | qs |
| Hydrogenated Lecithin | 90% to 0.001% | 10% to 0.001% |
| Caprylic/Capric Triglyceride | 90% to 0.001% | 5% to 0.001% |
| Pentylene Glycol | 90% to 0.001% | 5% to 0.001% |
| Shea Butter | 90% to 0.001% | 10% to 0.001% |
| Glycerin | 90% to 0.001% | 10% to 0.001% |
| Squalane | 90% to 0.001% | 1.0% to 0.001% |
| Ceramide 3 | 90% to 0.001% | 1% to 0.001% |
| Acetyl Hexapeptide-3 | 90% to 0.001% | 10% to 0.001% |
| Phospholipids | 90% to 0.001% | 5% to 0.001% |
| Hyaluronic Acid | 90% to 0.001% | 5% to 0.001% |
| Acetyl Glutamyl Heptapeptide | 90% to 0.001% | 10% to 0.001% |
| Palmitoyl Tripeptide-3 | 90% to 0.001% | 10% to 0.001% |
| Retinyl Paimitate | 90% to 0.001% | 1% to 0.001% |
| Pantothenic Acid | 90% to 0.001% | 1% to 0.001% |
| Ascorbyl Palmitate | 90% to 0.001% | 5% to 0.001% |
| Tocopheryl Acetate | 90% to 0.001% | 5% to 0.001% |
| Ectoin | 90% to 0.001% | 0.2% to 0.001% |
| Sea Whip Extract | 90% to 0.001% | 1% to 0.001% |
| Betaine | 90% to 0.001% | 2% to 0.001% |
| *Nelumbo Nucifera* (Sacred Lotus) Seed Extract | 90% to 0.001% | 10% to 0.001% |
| *Pinus Strobus* Bark Extract | 90% to 0.001% | 5% to 0.001% |
| Xanthan Gum | 90% to 0.001% | 1% to 0.001% |
| Propylene Glycol | 90% to 0.001% | 5% to 0.001% |
| Diazolidinyl Urea | 90% to 0.001% | 0.5% to 0.001% |
| Methylparaben | 90% to 0.001% | 0.2% to 0.001% |
| Propylparaben. | 90% to 0.001% | 0.2% to 0.001% |

Anti-Wrinkle Skin Rejuvenating Serum

| Ingredient | Quantity | Preferred Quantity |
| --- | --- | --- |
| Water | qs | qs |
| Diazolidinyl Urea | 90% to 0.001% | 0.30% to 0.001% |
| Methylparaben | 90% to 0.001% | 0.25% to 0.001% |
| Hydroxyethylcellulose | 90% to 0.001% | 0.3% to 0.001% |
| Stearamidopropyl Dimethylamine Lactate | 90% to 0.001% | 5% to 0.001% |
| Glycerin | 90% to 0.001% | 5% to 0.001% |
| Cetyl Alcohol | 90% to 0.001% | 4% to 0.001% |
| Glycol Stearate | 90% to 0.001% | 5% to 0.001% |
| Tocotrienols | 90% to 0.001% | 5% to 0.001% |
| Fibroblast Growth Factor | 90% to 0.001% | 10% to 0.001% |
| Stem Cell Factors | 90% to 0.001% | 10% to 0.001% |
| Vitamin C | 90% to 0.001% | 10% to 0.001% |
| Propylparaben | 90% to 0.001% | 0.2% to 0.001% |
| *Nelumbo Nucifera* (Sacred Lotus) Seed Extract | 90% to 0.001% | 10% to 0.001% |
| Phospholipids | 90% to 0.001% | 5% to 0.001% |
| Hyaluronic Acid | 90% to 0.001% | 5% to 0.001% |
| Algae Extract | 90% to 0.001% | 5% to 0.001% |

In the foregoing description, certain terms have been used for brevity, clearness and understanding; but no unnecessary limitations are to be implied therefrom beyond the requirements of the prior art, because such terms are used for descriptive purposes and are intended to be broadly construed. Moreover, the description and illustration of the invention is by way of example, and the scope of the invention is not limited to the exact details shown or described.

This invention has been described in detail with reference to specific embodiments thereof, including the respective best modes for carrying out each embodiment. It shall be understood that these illustrations are by way of example and not by way of limitation.

What is claimed is:

1. A topical composition comprising:
    (a) a topical base formulation from about 10-99.999% inclusive by weight of the topical composition wherein the topical base formulation comprises at least one of glycerin, triglyceride, natural butters, oils or waxes; and
    (b) active ingredients from about 0.001-90% inclusive by weight of the topical composition, wherein the active ingredients include:
        (i) stem cells and stem cell factors; and
        (ii) basic fibroblast growth factor, wherein the stem cells and stem cell factors are 5.4% by weight of the topical composition, and the basic fibroblast growth factor is 1% by weight of the topical composition; and wherein the active ingredients are combined in the topical base formulation for application to a user's skin.

2. The composition of claim 1 wherein the active ingredients are directly added to the topical base formulation.

3. The composition of claim 1 wherein the active ingredients are added to the topical base formulation in liposomal form.

4. The composition of claim 1 wherein the active ingredients are added to the topical base formulation in nanospherical form.

5. The composition of claim 1, further comprising from about 0.001% to about 89.999% inclusive by weight of at least one antioxidant selected from the group consisting of:
    (a) Tocotrienols;
    (b) Coenzyme Q 10;
    (c) Alpha Lipoic Acid;
    (d) Carnosine;
    (e) Glutathione;

(f) Superoxide Dismutase;
(g) Catalase;
(h) Pine Bark;
(i) Grape Seed;
(j) Onion;
(k) Blueberry;
(l) Apple Extract;
(m) Green Tea; and
(n) *Gorgonian* Extract.

6. The composition of claim 1, further comprising from about 0.001% to about 89.999% inclusive of at least one compound selected from the group consisting of:
(a) Acetyl Hexapeptide-8;
(b) Acetyl Tetrapeptide-5;
(c) Pentapeptide-3;
(d) Hydrolyzed Vegetable Protein;
(e) Tripeptide-3;
(f) Hexapeptide-10;
(g) Acetyl Glutamyl Hexapeptide-6;
(h) Acetyl Glutamyl Hexapeptide-3;
(i) Pamitoyl Tripeptide-5;
(j) Dipeptide Diaminobutyrooyl Benzylamide Diacetate;
(k) Pentapeptide-3;
(l) Tripeptide-1;
(m) Acetyl Tetrapeptide-2;
(n) Acetyl Hexapeptide-1;
(o) Nonapeptide-1;
(p) Tripeptide-2;
(q) Hexapeptide-11;
(r) Dipeptide-2;
(s) Carnosine;
(t) Palmitoyl Oligopeptide;
(u) Palmitoyl Tetrapeptide-7;
(v) Cottonseed Peptide; and
(w) Sweet Almond Peptide.

7. The composition of claim 1, further comprising at least one vitamin from about 0.001% to about 89.999% inclusive by weight of the topical composition, wherein the at least one vitamin is selected from the group consisting of:
(a) Vitamin A;
(b) Retinol;
(c) Vitamin $B_1$;
(d) Vitamin $B_2$;
(e) Vitamin $B_3$;
(f) Vitamin $B_5$;
(g) Vitamin $B_6$;
(h) Vitamin $B_{12}$;
(i) Panthenol;
(j) Vitamin C;
(k) Vitamin D;
(l) Vitamin E;
(m) Beta Carotene;
(n) Lycopene; and
(o) Lutein.

8. The composition of claim 1, further comprising from about 0.001% to about 89.999% inclusive of at least one component selected from the group consisting of:
(a) *Nelumbu Nucifera* (Sacred Lotus) and its seeds, roots, rhizomes, flower, petals, pistules or any part thereof;
(b) Blue Lotus and its roots, seeds, rhizomes, flowers, petals, pisstules, or any part thereof;
(c) White Lotus and its roots, seeds, rhizomes, flowers, petals, pisstules, or any part thereof;
(d) Pink Lotus and its roots, seeds, rhizomes, flowers, petals, pisstules, or any part thereof;
(e) Yellow Lotus and its roots, seeds, rhizomes, flowers, petals, pisstules, or any part thereof;
(f) *Lotus Japonica;*
(g) Estrogen;
(h) Estriol;
(i) Estradiol;
(j) Progesterone;
(k) Pregenolone;
(l) Testosterone; and
(m) Phytoestrongens from Soy, Resveratrol, Red Clover, Wild Yarn, or *Polygonum Cuspidatum.*

9. The composition of claim 1, further comprising from about 0.001% to about 89.999% inclusive of at least one component used in typical skin care formulas selected from the group consisting of:
(a) Glycerine;
(b) Alcohol;
(c) Alpha hydroxy acids;
(d) Lactic acid;
(e) Glycolic acid;
(f) Citric acid;
(g) Malic acid;
(h) Soybean oil;
(i) Sunflower seed oil;
(j) Safflower seed oil;
(k) Palm oil;
(l) Almond oil;
(m) Olive oil;
(n) Ginseng;
(o) Rapeseed oil;
(p) Avocado oil;
(q) Lecithin;
(r) Shea butter;
(s) Squalane;
(t) Xanthan gum;
(u) Propylene glycol;
(v) Aloe;
(w) Isopropyl myristate;
(x) Cetyl alcohol;
(y) Butylene glycol;
(z) *Centella asiatica;*
(aa) *Echinacea purpurea;*
(bb) Glycol stearate;
(cc) Cocoa seed butter;
(dd) Carbomer;
(ee) Ceramides;
(ff) Phenyl trimethicone;
(gg) Dimethicone;
(hh) Silicon;
(ii) Polysilocilane;
(jj) Macadamia Nut oil;
(kk) Seaweed extract;
(ll) Algae extract;
(mm) Fucoidan;
(nn) *Laminaria Japonica;*
(oo) *Gracileria Ferox;*
(pp) *Laminaria Digitata;* and
(qq) *Caulerpa taxifolia.*

10. The composition of claim 1, further comprising from about 0.001% to about 89.999% inclusive of at least one component selected from the group consisting of:
(a) Sunscreen agents;
(b) Wheat Peptide;
(c) Oat Peptide;
(d) Soy Peptide;
(e) Ectoin;
(f) Methylsulfonylmethane (MSM);
(g) S-adenosylmethionine;
(h) Chondroitan Sulfate;

(i) Chitin/chitosan;
(j) Glucosamine;
(k) Tumeric;
(l) Menthol;
(m) Glutamine;
(n) Trimethyl Glycine;
(o) Aloe;
(p) Capsaicin; and
(q) Keratan Sulfate.

11. The composition of claim 1, further comprising from about 0.001% to about 89.999% inclusive of at least one amino acid selected from the group consisting of:
(a) Alanine;
(b) Arginine;
(c) Aspartate;
(d) Asparagines;
(e) Cysteine;
(f) Glycine;
(g) Lysine;
(h) Valine;
(i) Leucine;
(j) Histidine;
(k) Methionine;
(l) Prolinel Hydroxyproline;
(m) Serine;
(n) Ornithine;
(o) Glutamine;
(p) Ornithine;
(q) Tyrosine; and
(r) Tryptophane.

12. The composition of claim 1 further comprising hyaluronic acid from about 0.001% to 89.999% inclusive by weight of the topical composition.

13. A method of regenerating integument cells comprising applying a topical composition as disclosed in claim 1 to the integument of a person.

14. The method of claim 13 wherein the topical composition used further comprises from about 0.001% to about 89.999% inclusive by weight of at least one antioxidant selected from the group consisting of;
(a) Tocotrienols;
(b) Coenzyme Q 10;
(c) Alpha Lipoic Acid;
(d) Carnosine;
(e) Glutathione;
(f) Superoxide Dismutase;
(g) Catalase;
(h) Pine Bark;
(i) Grape Seed;
(j) Onion;
(k) Blueberry;
(l) Apple Extract;
(m) Green Tea; and
(n) Gorgonian Extract.

15. The method of claim 13 wherein the regeneration of integument cells is for the purpose of reducing signs of aging of a skin.

16. The method of claim 13 wherein the regeneration of integument cells assists wound healing and the reduction of scar tissue.

17. The composition of claim 1, further comprising at least one component selected from the group consisting of:
1 Hyaluronan;
2 Epidermal Growth Factor;
3 Insulin-like Growth Factor;
4 Acidic Fibroblast Growth Factor;
5 Fibroblast Growth Factor-10;
6 Nerve Growth Factors; and
7 Human Growth Hormone.

* * * * *